(12) United States Patent
Gere et al.

(10) Patent No.: US 7,277,120 B2
(45) Date of Patent: Oct. 2, 2007

(54) STEREO IMAGING SYSTEM AND METHOD FOR USE IN TELEROBOTIC SYSTEMS

(75) Inventors: David Gere, Menlo Park, CA (US); Christopher R. Burns, South San Francisco, CA (US); John D. Stern, Menlo Park, CA (US); Michael J. Tierney, Pleasanton, CA (US)

(73) Assignee: Intuitive Surgical, Inc, Sunnyvale, CA (US)

( * ) Notice: Subject to any disclaimer, the term of this patent is extended or adjusted under 35 U.S.C. 154(b) by 149 days.

(21) Appl. No.: 10/795,963

(22) Filed: Mar. 7, 2004

(65) Prior Publication Data

US 2006/0092273 A1    May 4, 2006

Related U.S. Application Data

(62) Division of application No. 09/378,173, filed on Aug. 20, 1999, now Pat. No. 6,720,988.

(60) Provisional application No. 60/111,714, filed on Dec. 8, 1998.

(51) Int. Cl.
*A61B 1/04* (2006.01)
*H04N 13/00* (2006.01)

(52) U.S. Cl. .............. 348/45; 348/51; 348/65; 382/154

(58) Field of Classification Search ........... 348/42, 348/51; 359/462; 382/154, 294
See application file for complete search history.

(56) References Cited

U.S. PATENT DOCUMENTS 4,562,463 A    12/1985    Lipton
4,583,117 A    4/1986    Lipton et al.
4,651,201 A    3/1987    Schoolman
4,724,480 A  * 2/1988    Hecker et al. ............... 348/95
4,862,873 A    9/1989    Yajima et al.
4,873,572 A    10/1989    Miyazaki et al.
5,175,694 A    12/1992    Amato (Continued)

OTHER PUBLICATIONS

Vertut, Jean and Coeffet, Philippe Coiffet; "Robot Technology; vol. 3A Teleoperation and Robotics Evolution and Development"; 1986; Prentice-Hall, Inc; Englewood Cliffs, N.J.

*Primary Examiner*—Gims Philippe
*Assistant Examiner*—Erick Rekstad

(57) ABSTRACT

This invention relates to a stereo imaging system for use in telerobotic systems. A method of imaging a target site in a stereo imaging system is provided. The method typically includes capturing a right and a left optical image of the target site and transforming the right and the left optical images preferably into digital information. The method further includes converting the digital information into opposed images of the target site displayed on a stereo display of the stereo imaging system, one of the opposed images being associated with the right optical image and the other of the opposed images being associated with the left optical image. The method further includes regulating the digital information to cause the positions of the target site displayed on the opposed images to change relative to each other. The invention further provides for a method of aligning the opposed images, to a method of adjusting the stereo working distance of an image capture device, such as an endoscope and to a stereo imaging system.

17 Claims, 12 Drawing Sheets

U.S. PATENT DOCUMENTS

| | | |
|---|---|---|
| 5,315,630 A * | 5/1994 | Sturm et al. ................... 378/65 |
| 5,368,015 A | 11/1994 | Wilk |
| 5,402,801 A | 4/1995 | Taylor |
| 5,417,210 A | 5/1995 | Funda et al. |
| 5,577,991 A | 11/1996 | Akui et al. |
| 5,591,119 A | 1/1997 | Adair |
| 5,613,013 A * | 3/1997 | Schuette ..................... 382/124 |
| 5,776,049 A | 7/1998 | Takahashi |
| 5,792,045 A | 8/1998 | Adair |
| 5,860,912 A | 1/1999 | Chiba |
| 5,864,359 A | 1/1999 | Kazakevich |
| 6,191,809 B1 * | 2/2001 | Hori et al. .................... 348/45 |
| 6,335,755 B1 | 1/2002 | McLaine |

* cited by examiner

STEREO IMAGING SYSTEM AND METHOD FOR USE IN TELEROBOTIC SYSTEMS

CROSS REFERENCE TO RELATED APPLICATIONS

This application is a divisional of U.S. Ser. No. 09/378,173, filed on Aug. 20, 1999, now U.S. Pat. No. 6,720,988, which claims the benefit of priority from U.S. Ser. No. 60/111,714, filed Dec. 8, 1998, the full disclosures of which are incorporated herein by reference.

BACKGROUND OF THE INVENTION

This invention relates to stereo imaging systems, devices, and methods. In particular, the invention relates to a method of imaging a target site with a stereo imaging system, a method of aligning images of a stereo imaging system, a method of adjusting the stereo working distance of a stereo imaging system, and a stereo imaging system.

In minimally invasive surgery such as laparoscopic surgery, for example, a patient's abdomen is insufflated with gas, and trocar sleeves or cannulas are passed through small incisions to provide entry ports for laparoscopic surgical instruments. The laparoscopic surgical instruments generally include an endoscope in the form of a laparoscope for viewing the surgical site or field and surgical instruments defining end effectors such as clamps, graspers, scissors, staplers, and needle holders. The surgical instruments are similar to those used in conventional (open) surgery, except that the working end of each tool is separated from its handle by an elongate shaft. To perform surgical procedures, the surgeon passes instruments through the trocar sleeves and manipulates them from outside the abdomen by sliding them in and out through the sleeves in the abdominal wall, and actuating end effectors on distal ends of the instruments, while viewing the surgical site through the laparoscope.

In robotically-assisted and telerobotic surgery (both open and endoscopic procedures), the position of the surgical instruments is typically controlled by servo motors rather than directly by hand. The servo motors follow the motions of a surgeon's hands as he or she manipulates input or master control devices whilst remotely viewing the operation via an image displayed on a viewer, the viewer being operatively linked to an image capture device typically in the form of an endoscope. The viewer and its associated image capture device form part of an imaging system. The servo motors are typically part of an electromechanical surgical apparatus, which typically includes robotic arms that support and control the surgical instruments that have been introduced into e.g. an open surgical site, or through trocar sleeves into a body cavity, such as the patient's abdomen, or the like. During the operation, the master control devices provide mechanical actuation and control of a variety of surgical instruments. Such surgical instruments can typically include tissue graspers, needle drivers, etc., that can perform various surgical procedures for the surgeon, i.e., holding or driving a needle, grasping a blood vessel, dissecting tissue, and the like, while the surgeon views the procedures on the viewer.

It will be appreciated that the imaging system should meet certain criteria to render it suitable for use in applications such as minimally invasive surgical applications. In particular, the image displayed to the surgeon should be clear and optically correct. Furthermore, the imaging system should provide an adequate field of view and adequate resolution and brightness, so as to enable the surgical field to be adequately visualized by the surgeon.

Stereo endoscopes are sometimes used to provide the surgeon with a stereo image at the viewer. Stereo endoscopes are typically arranged to have a fixed point of intersection between two viewing axes. The distance between the fixed point and an object viewing end of the endoscope is referred to as the "working distance" of the endoscope. In use, the surgeon, whilst performing a surgical procedure, may want to observe an object removed from the point of intersection. For example, when using the endoscope to "search" for the surgical site, the surgeon typically observes objects at a working distance beyond the point of intersection. When the surgical site is reached, he or she may want to observe objects which are closer to the viewing end of the endoscope or beyond the point of intersection when the surgical procedure is actually performed.

Additionally, stereo endoscopes are not always precisely optically aligned due to, e.g., manufacturing constraints, and the like. In other words, the viewing axes sometimes do not intersect either precisely or at all. When such an endoscope is used, without compensating for such misalignment of the viewing axes, it could lead to the surgeon experiencing premature eye strain, headache, and/or general fatigue in attempting to compensate for the imprecise "stereo image". Compensating for such misalignment should increase the time between when a surgeon commences a surgical procedure and when he or she becomes tired and thus less efficient at performing the procedure. Accordingly, it should enhance the overall comfort of the surgeon, enabling the surgical procedure to be performed in a more precise manner, by enhancing the optical comfort experienced by the surgeon during a surgical procedure.

It is an object of this invention to provide an imaging system which provides for adjustment of the working distance of a stereo endoscope. It is also an object of this invention to provide an imaging system which provides for alignment of the viewing axes of such a stereo endoscope. Further objects will be apparent from the following description of the preferred embodiments of the invention.

SUMMARY OF THE INVENTION

According to one preferred aspect of the invention, there is provided a method of imaging a target site with a stereo imaging system. The method comprises capturing a right and a left optical image of the target site. It further includes transforming the right and the left optical images into regulatable information, converting the regulatable information into opposed images of the target site displayed in a stereo display of the stereo imaging system, one of the opposed images being associated with the right optical image and the other of the opposed images being associated with the left optical image, and regulating the regulatable information to cause the position of the target site displayed on the opposed images to change relative to each other.

According to another preferred aspect of the invention, there is provided a method of aligning opposed images of a stereo imaging system. The method comprises capturing a right and a left optical image of a target site, transforming the right and the left optical images into digital information in the form of digital arrays associated with each of the right and the left optical images, converting the digital information associated with each digital array into opposed images of the target site displayed on a stereo display of the stereo imaging system, and isolating a portion of at least one digital array so that only digital information associated with the isolated portion of that array is converted into an associated image, the isolated portion being selected so as to align the opposed images displayed on the stereo display.

According to yet another preferred aspect of the invention, there is provided a method of adjusting the stereo working distance of a stereo imaging system. The method comprises capturing a right and a left optical image of a target site, transforming the right and the left optical images into digital information in the form of digital arrays associated with each of the right and the left optical images, converting the digital information associated with each digital array into opposed images of the target site displayed on a stereo display of the stereo imaging system, and isolating a portion of at least one digital array so that only digital information associated with the isolated portion of that array is converted into an associated image, the isolated portion being selected to cause the working distance to vary.

According to yet a further preferred aspect of the invention, there is provided a stereo imaging system comprising a stereo image capture device for capturing a right and a left optical image of a target site. The system further includes an image transformer operatively associated with the image capture device for transforming the right and the left optical images into corresponding regulatable information, two display areas operatively associated with the image transformer for displaying a right and a left image derived from the corresponding regulatable information, and a processor arranged to regulate the regulatable information to cause the positions of the target site displayed on the opposed images to change relative to each other.

Advantageously, the regulatable information is in the form of digital information.

According to yet a further preferred aspect of the invention, there is provided a method of imaging a target site with a stereo imaging system. The method comprises capturing first and second optical images of the target site as regulatable information, the first and second optical images defining a positional relationship, manipulating the regulatable information to define an altered positional relationship, and converting the manipulated regulatable information into left and right images of the target site and displaying the left and right images on a stereo display of the stereo imaging system.

According to yet another preferred aspect of the invention, there is provided a method of aligning opposed images of a stereo imaging system. The method comprises capturing a right and a left optical image of a target site, transforming the right and the left optical images into regulatable information associated with each of the right and left optical images, converting the regulatable information into images of the target site displayed on a stereo display of the stereo imaging system, and regulating the regulatable information to align the images displayed on the stereo display.

According to yet another preferred aspect of the invention, there is provided a method of adjusting the stereo working distance of a stereo imaging system. The method comprises capturing a right and a left optical image of a target site, transforming the right and the left optical images into regulatable information associated with each of the right and the left optical images, converting the regulatable information into images of the target site displayed on a stereo display of the stereo imaging system, and regulating the regulatable information to adjust the stereo working distance of the stereo imaging system.

According to yet another preferred aspect of the invention, there is provided a method of producing a stereo image of a site at a predetermined position, the method comprising aiming a viewing end of a stereo endoscope at the site so that the first image of the site is passed along a first optical path of the stereo endoscope and a second image of the site is passed along another optical path of the stereo endoscope. The method further comprises converting said first and second images into corresponding first and second sets of electronically readable information, causing the first set of electronically readable information to be transferred into a first visual image on a first display area, causing the second set of electronically readable information to be transferred into a second visual image on a second display area, and directing the images from the display areas to the predetermined position so that, at the predetermined position, the images together form a stereo image viewable by an operator.

BRIEF DESCRIPTION OF THE DRAWINGS

The foregoing and other objects, features and advantages of the invention will be apparent from the following more particular description of preferred embodiments and features of the invention and with reference to the drawings. It will be appreciated that the drawings are schematic and merely serve to illustrate the principles of the invention. In the drawings.

DESCRIPTION OF THE SPECIFIC EMBODIMENTS

Figure 1:
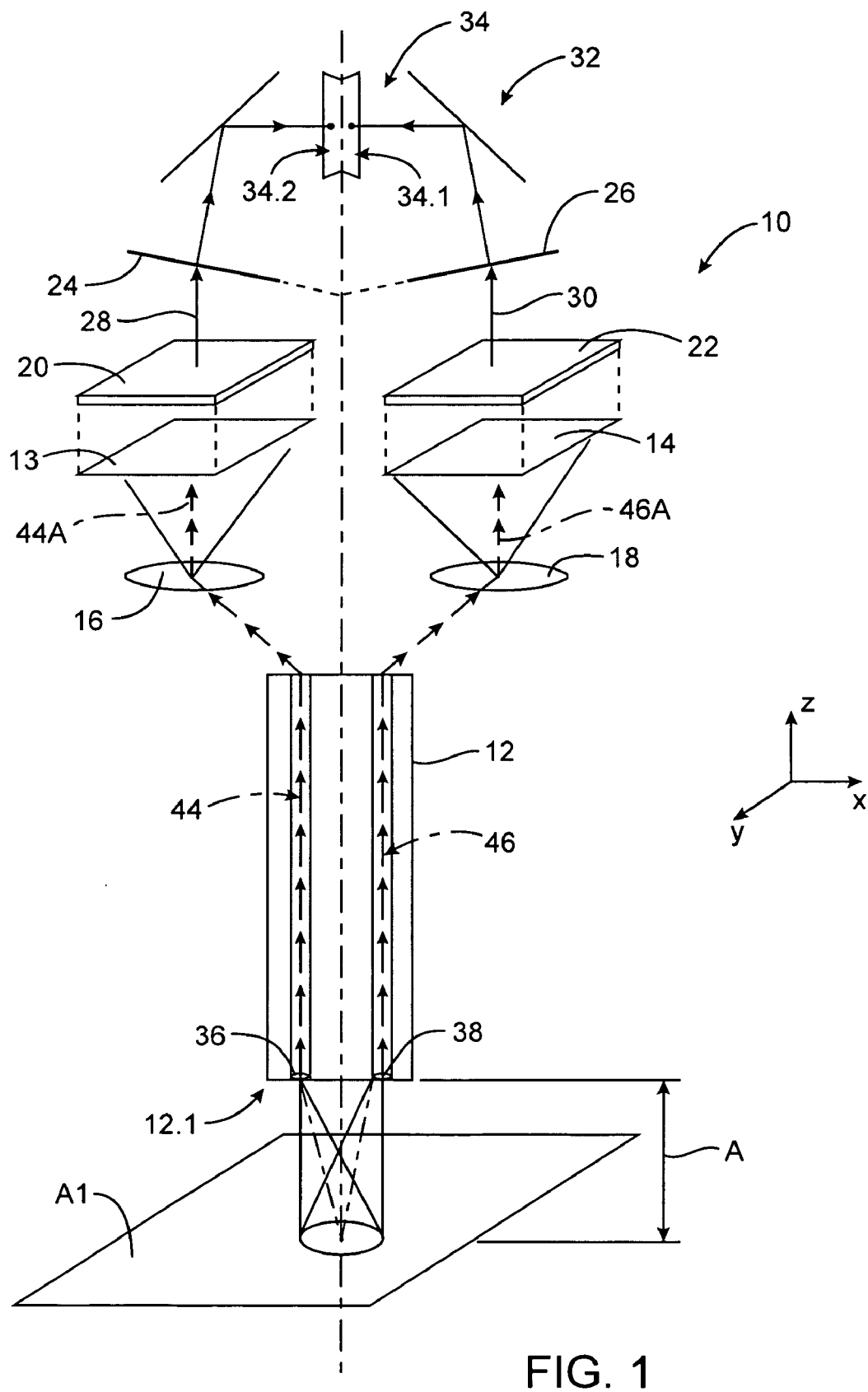
FIG. 1 shows a schematic three-dimensional view of one embodiment of an imaging system in accordance with the invention.

Referring to the drawings, and with specific reference to FIG. 1, an imaging system, in accordance with the invention, is generally indicated by reference numeral 10.

While the preferred embodiments of the present invention are described as including converting the various optical images into regulatable information in the form of digital information, other forms of regulatable information could also be used, such as, for example, analogue information from a video and a sync signal, as will be apparent to one of ordinary skill in the art upon reading this disclosure.

Although throughout the rest of this specification the invention will be described with reference to its application in a minimally invasive surgical apparatus employing an image capturing device in the form of an endoscope, it is to be understood that the field of the invention is not necessarily limited to this application. Accordingly, the invention can be used in, e.g., open surgery, also.

The system 10 includes a stereo imaging device in the form of a stereo endoscope 12, for example. The system 10 further includes two Charge Coupled Devices (CCDs) 13 and 14, optical lenses 16 and 18, and read means 20, 22 for reading the CCDs and converting information read on the CCDs into a digital format. The read means 20, 22 is typically an appropriate electronically driven system such as a Camera Control Unit (CCU) that transforms optical information read by the CCDs 20, 22 into digital format. The CCD and CCU arrangements can be of the type available from Panasonic™ under the part nos.: GP-US522/GP-US532 3CCD color CCU. Accordingly, an electronic processor (not shown) is typically in operative communication with the read means 20, 22. The system 10 yet further includes two display stations, e.g., in the form of Cathode Ray Tubes (CRTs) schematically indicated at 24, 26, each of which is operatively connected to one of the read means 20, 22 as indicated by lines 28, 30 so as to convert preferably digitally formatted information received from the read means 20, 22 into corresponding visual images on the CRTs 24, 26. It is to be appreciated that although reference is made to Cathode Ray Tubes, any other appropriate display station or visual screening apparatus can be used, e.g., a liquid crystal display, or the like. An assembly of reflecting surfaces or a reflective train, e.g., comprising mirrors, or the like, is generally indicated by reference numeral 32. The assembly 32 conveys the images from the CRTs 24, 26 to a viewer at 34. It will be appreciated that the direction of view at 34 is normal to the page, a right eye image being indicated at 34.1, and a left eye image being indicated at 34.2 for example.

Figure 2:
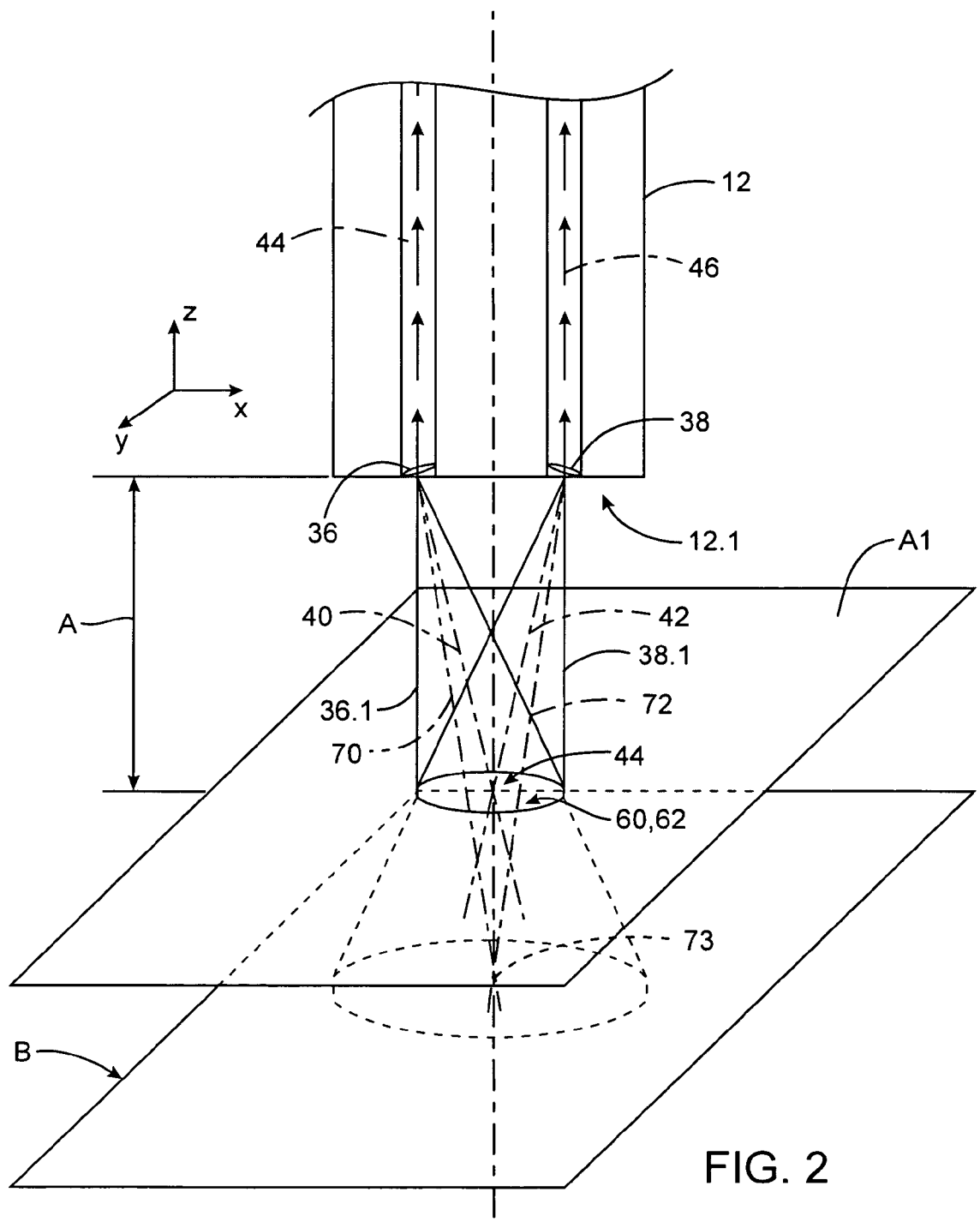
FIG. 2 shows a schematic three-dimensional view of an object viewing end portion of an endoscope of the system shown in FIG. 1.

As can best be seen with reference to FIG. 2, in which the same reference numerals as used in FIG. 1 represent the same parts unless otherwise stated, the stereo endoscope 12 includes two optical lenses 36, 38. The optical lenses 36, 38 have viewing axes as indicated by lines 40, 42. The lenses 36, 38 are fixed in position so that the axes 40, 42 intersect at 44. If an object is viewed at a working distance generally corresponding to the intersection 44, namely on a plane at A, the object is viewed generally at an optically correct working distance. The further the object is removed from the intersection 44, the more optically incorrect the object is viewed. Accordingly, should the object be generally at another plane relative to the endoscope 12, such as the plane indicated at B, the object would not be viewed optically correctly through the endoscope 12 since the object is not at the working distance A of the endoscope, namely at the intersection 44. Furthermore, the greater the positional deviation of the object sought to be viewed through the endoscope 12 relative to the intersection 44, the more optically incorrect the viewed stereo image becomes.

As mentioned earlier, it is often required to view an object at varying distances relative to an object viewing end 12.1 of the endoscope 12. For example, during endoscopic surgery, a surgeon often desires to view objects beyond A when introducing the endoscope 12 into a patient's body so as to locate a predetermined surgical site within the body and then may need to view objects at other working distances, which can be positioned closer to the viewing end 12.1 than the distance A, or beyond the intersection corresponding to working distance A, when the surgical site is located and the surgical procedure is to be performed. The system 10 is arranged to adjust the working distance of the endoscope 12, i.e., by effectively changing the distance of the intersection 44 relative to the object viewing end 12.1 of the endoscope 12.

As can best be seen with reference to FIG. 2, a viewing area, or the field of view, of each lens 36, 38 can be represented by a section through an imaginary conical volume indicated by referenced numerals 36.1, 38.1. If an object is on a plane at A, as indicated at A1, within the bounds of the optical field of view, as indicated by the oval shaped areas 60, 62, the object is viewed at an optically correct working distance. It will be appreciated that the axes 40, 42 are positioned at the centers of the oval shaped areas 60, 62 in an optically aligned system. The areas 60, 62 are illustrated as being coincident. However, in the case of an optically misaligned stereo endoscope, the areas would not be coincident, and the axes would not intersect at 44, but would be offset relative to each other.

Images of an object viewed at A are passed through the lenses 36, 38, along optical paths indicated by arrows 44, 46 in the endoscope 12, and are then magnified through lenses 16, 18 and are then projected onto optically sensitive surfaces of e.g., the CCDs 13, 14, as indicated by arrows 44A, 46A in FIG. 1.

Figure 3:
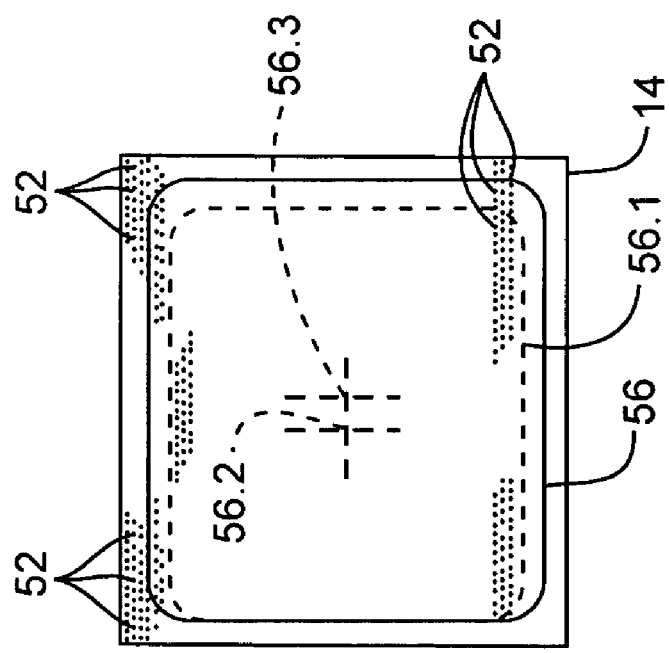
FIG. 3 shows a schematic plan view of two Charge Coupled Devices (CCDs) of the system shown in FIGS. 1 and 2, each CCD being operatively associated with a separate display monitor.
Figure 3:
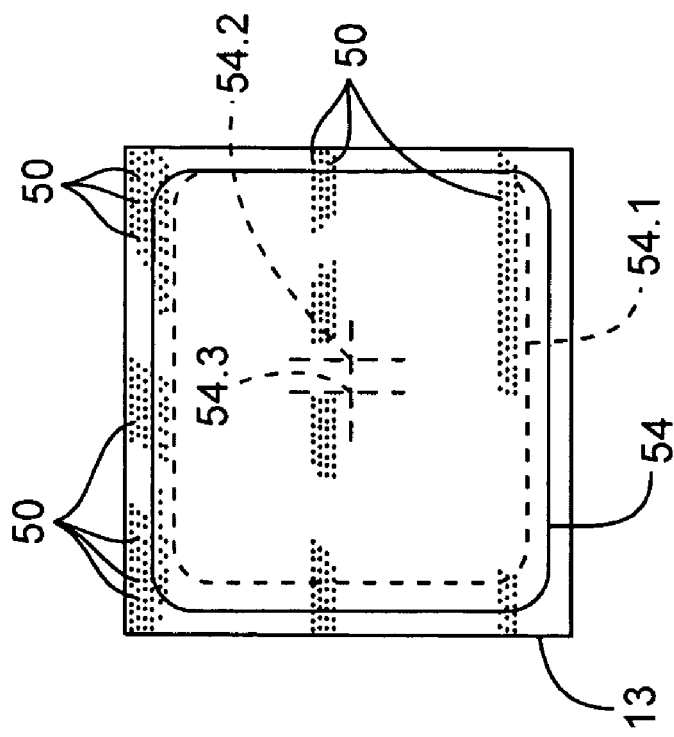
Figure 3:
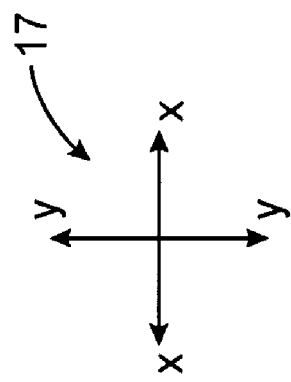

As can best be seen with reference to FIG. 3, the CCDs 13, 14 each include an array of photosensitive pixels schematically indicated by the dots 50, 52. The images from the lenses 16, 18, are projected onto the photosensitive surfaces of the CCDs 13, 14, respectively. A predetermined portion of the images represented by cropping windows 54, 56 is read by the read means 20, 22. Only a portion of each image, namely the cropping windows 54, 56, is read, so as to avoid peripheral distortions at the outer region of the viewing areas 60, 62. The read means 20, 22 reads the information from the photosensitive surfaces of the CCDs 13, 14, converts the information into preferably a digital format and transmits the digital information to the CRTs 24,26 so as to cause the information to form corresponding images on the CRTs 24,26.

A method employed by the system 10 to vary the working distance of the endoscope includes causing the read means 20, 22 to read only a selected or isolated portion of the cropping windows 54, 56 along an X axis of the coordinate frame indicated at 17. Thus, by way of example, should it be required to increase the working distance beyond of the intersection 44 of the endoscope 12 the read means 20, 22 is caused to read inner portions of the cropping windows 54, 56, namely portions 54.1, 56.1 only, as can best be seen in FIG. 3. It will be seen that the distance between the centers 54.2, 56.2 of the cropping windows 54.1, 56.1 are closer to each other along the X axis than is the case with the centers 54.3 and 56.3 of the cropping windows 54, 56. The centers 54.2, 56.2, 54.3, and 56.3 determine the eventual viewing axes. Thus, where the full cropping windows 54, 56 are read, the centers 54.3, 56.3 correspond to viewing axes 40, 42. Where cropping windows 54.1, 56.1 are read, the centers 54.2, 56.2 correspond with viewing axes which intersect at a point further away from the viewing end 12.1 of the endoscope 12 than the intersection 44 and, for example, viewing axes 70, 72 which intersect at 73 on a plane B, with reference to FIG. 2 of the drawings, can be achieved. It will be appreciated that whether the viewing axes corresponding with the centers 54.2, 56.2 of the cropping windows 54.1, 56.1 intersect at a point further away from or closer to the viewing end 12.1 depends on the system configuration e.g. the optic lens arrangement, used in the endoscope. Naturally, should portions of the cropping windows 54, 56 be selected which define centers further removed from each other along the X axis, the opposite is true. In this way, an object at a working distance differing from the working distance set by the lenses 36, 38, for example on the plane B, can be viewed in a more optically correct manner, by varying the working distance as hereinbefore described.

It will be appreciated that the selected or isolated portions of the cropping windows 54, 56 are converted into corresponding visual images on the CRTs 24, 26. The smaller the portion of the cropping windows 54, 56 selected, the smaller the amount of pixel information defining the visual images displayed on the CRTs 24, 26 becomes, which negatively effects picture clarity. Thus, to preserve picture clarity the selected cropping window portions should not be too small. This can best be illustrated with reference to FIG. 3. In FIG. 3, it will be seen that the number of pixels 50, 52 in the cropping windows 54, 56 is greater than that in the cropping windows 54.1, 54.2. Thus the resultant images on the CRTs 24, 26 are then derived from less information, which negatively effects picture quality. Accordingly, a stage is reached where increased variation of the working distance and corresponding sacrifice of picture clarity is not viable.

In the imaging system 10, isolating portions of the cropping areas 54, 56 as described above is used also in a method of aligning the images displayed on the CRTs 24, 26 in the case of misalignment. In the endoscope 12, as already mentioned, it can happen that e.g., the lenses 36, 38, are not perfectly aligned. This can occur as a result of manufacturing constraints, or the like. In such a case, the axes 40, 42 may not intersect but can be marginally offset relative to each other on an X-Y plane. To compensate for misalignment of the axes 40, 42 in accordance with the method of the invention, a target in the form of a cross, for example, is positioned at a predetermined distance from the viewing end 12.1 of the endoscope 12, such as at the working distance A of the endoscope 12. This can be achieved by a suitable set piece or target device (not shown) releasably locatable on the viewing end 12.1 of the endoscope 12 so that the target or cross is at a specific distance relative to the end 12.1 of the endoscope 12. The images passed along the respective optical paths 44, 46 are typically colored so that the image passed along path 20 is green, for example, and the image passed along path 22 is magenta, for example. In the case of misalignment, the crosses viewed through the viewer at 34 would not be superimposed. It will be appreciated that distinctively coloring the images passing along the two optical paths is to assist in the aligning of the crosses displayed on the CRTs 24, 26 during alignment. Portions of the cropping areas 54, 56 are then selected to cause their centers to be moved along the X and Y axes until the crosses viewed through the viewer 34 are superimposed or in register. In such a condition the misalignment is compensated for. The area of the cropping windows are chosen to be as large as possible while maintaining the registration of the crosses as viewed to cause the images displayed at the viewer 34 to be derived from as much pixel information as possible, thereby to optimize picture quality. The chosen portions of the cropping windows are then set by the system 10 so that alignment is retained in use. The working distance can then selectively be varied by isolating cropping areas having centers at different spacings relative to each other along the X axis.

It has been found that misalignment of the axes 40, 42 can cause a user, e.g., a surgeon, to experience discomfort, e.g., eye strain, after a certain length of use. By compensating for misalignment as described above, the length of time before such discomfort is experienced is typically increased.

In accordance with another aspect of the invention, the endoscope system 10 includes means for focusing the resultant images on the CRTs. Focusing is achieved by mechanical means arranged to vary the relative distances between the lenses 16, 18 and their corresponding CCDs 13, 14. The mechanical means may be in any appropriate form. For example, the mechanical means may include a foot pedal, the surgeon adjusting focus by varying the inclination or degree of depression of such a foot pedal. Instead, or in addition, manually operable switches can be provided on a console or the like. The mechanical means can be motorized. An example of such focusing means is described hereinbelow with reference to FIG. 5 of the drawings.

It will be appreciated that in a surgical environment sterility is of cardinal importance. Since the endoscope is used in a surgical procedure, it should be sterilizable. It would be advantageous if the rest of the imaging system could be isolated from the endoscope to obviate having to sterilize the rest of the imaging system, and to permit the endoscope to be changed during a surgical procedure without contaminating the sterile environment.

Figure 4:
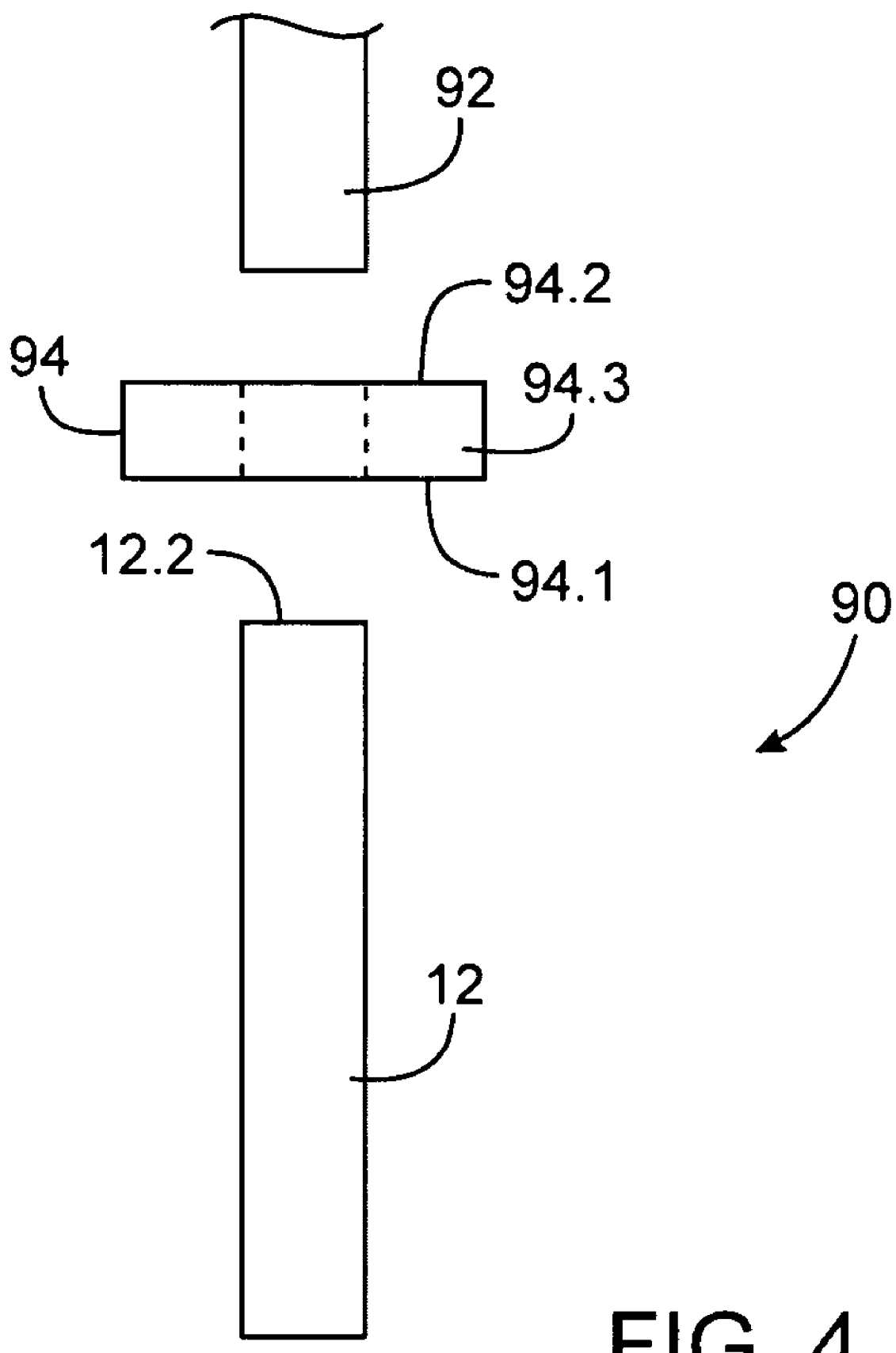
FIG. 4 shows a schematic representation of an isolating member in accordance with another aspect of the invention.

In FIG. 4, a forward or operative end portion of the imaging system 10 is generally indicated by reference numeral 90. The portion 90 includes the endoscope 12. The endoscope 12 is normally connected to a video camera arrangement or camera head including the CCDs and CCUs. Part of the camera head is schematically indicated by reference numeral 92. The imaging system 10 includes an isolating member 94. One end portion 94.1 of the member 94 is releasably couplable on an operative rear end 12.2 of the endoscope 12. This can be achieved by any appropriate complementary coupling formation on the rear end 12.2 and the end portion 94.1. The complementary coupling formations can be in the form of mating internal and external screw-threads on the end 12.2 and portion 94.1. An opposed end portion 94.2 of the member 94 is releasably couplable to the camera head 92. This can also be achieved by any appropriate complementary coupling formations.

The isolating member 94 can include an optically correct window to permit optical information to pass therethrough from the endoscope 12 to the camera head 92. A surgical drape is connectable around or onto a periphery 94.3 of the member 94. To this end the member 94 can include location means, e.g., a suitable peripheral surface, or the like, to enable adhesive tape to be adhesively secured thereon and to which a surgical drape can be releasably adhered. Alternatively, the member 94 can form an integral part of a surgical drape.

Accordingly, the endoscope system 10 includes a window member mountable at the end of the endoscope 12 remote from the lenses 36, 38. In use, a drape is located over the rest of the imaging system 10, and taped around the periphery 94.3 of the member 94. In this manner, the rest of the imaging system is isolated from a surgical procedure and accordingly need not be sterilized between procedures. Furthermore, since the drape and window assembly are sterile, any sterile objects that contact the drape or window assembly will remain sterile. This permits endoscopes to be changed repeatedly during the procedure without requiring a sterile camera head.

Figure 5:
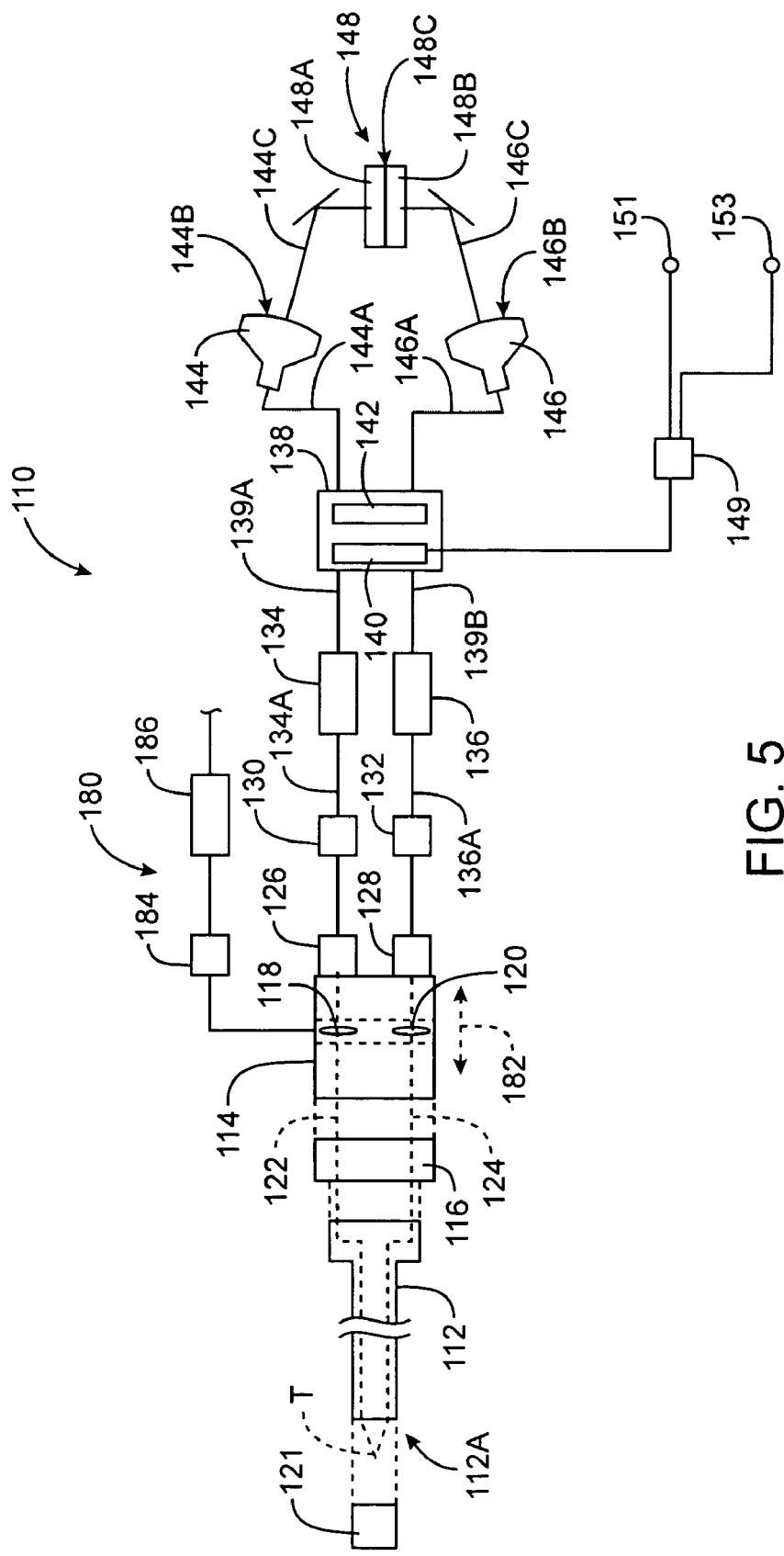
FIG. 5 shows a schematic view of another embodiment of an imaging system in accordance with the invention.

Referring now to FIG. 5 of the drawings, a preferred imaging system in accordance with the invention is generally indicated by reference numeral 110. The system 110 includes an image capturing device in the form of a stereo endoscope 112 having a viewing end 112A. The endoscope 112 is operatively connected to a camera head 114 by means of a coupler 116. The coupler 116 is arranged to enable the rest of the imaging system 110 to be isolated from the endoscope 112, as described above with reference to FIG. 4 of the drawings. Isolation of the rest of system 110 is typically achieved by means of a surgical drape positioned to cloak the rest of the system 110, the drape being secured to the coupler 116.

The camera head 114 typically includes two focusing lenses 118, 120 for focusing a right and left optical image relayed along optical paths 122, 124, respectively. The camera head 114 further includes two Charge Coupled Devices 126, 128 arranged to cooperate with the optical paths 122, 124. The right and left optical images are typically directed through the lenses 118, 120 onto photosensitive surfaces defined by the CCDs 126, 128. Camera Control Units 130, 132 are operatively connected to the CCDs 126, 128 so as to scan the photosensitive surfaces of the CCDs and to convert information derived from the scanned photosensitive surfaces into video format.

Video formatted information associated with the right optical image is then forwarded to a video processor 134 as indicated by line 134A. Similarly, video formatted information associated with the left optical image is forwarded to a video processor 136 as indicated by line 136A. The video processors 134, 136 process the video formatted information to enhance the information by e.g., decreasing electronic noise, enhancing edges to provide sharper or crisper images, and/or the like.

After the video formatted information associated with the right and the left optical images has been processed by the processors 134, 136, the information is forwarded to another video processor indicated by reference numeral 138. The information associated with the right and the left optical images is fed to the video processor 138 as indicated by lines 139A, 139B, respectively, and is typically in the form of digital information.

The video processor 138 includes an alignment and working distance compensation processing stage indicated by reference numeral 140. In the stage 140, the digital information sets associated with the right and the left optical images are each arranged in the form of a digital information array as indicated schematically in FIG. 7 of the drawings, and as described in greater detail hereinbelow. To facilitate alignment of the right and the left images and working distance adjustment of the endoscope 112 the digital information is regulated as described hereinbelow.

After the stage at 140, the regulated digital information is scanned at a scan conversion stage 142 to procure associated analog information displayable on e.g., Cathode Ray Tube monitors. After the scanning stage 142, the analog information associated with the right optical image is forwarded to a monitor 144 and the analog information associated with the left optical image is forwarded to a monitor 146, as indicated by lines 144A, 146A, respectively. At the monitors 144, 146, the information forwarded along lines 144A, 146A is used to form opposed images each of which is displayed on a monitor display 144B, 146B of the monitors 144, 146. The images displayed on the monitor displays 144B, 146B are then guided along optical paths 144C, 146C to a viewer at 148. The viewer 148 typically includes two opposed reflective surfaces 148A, 148B for directing the optical paths 144C, 146C in generally parallel directions to be observed separately by each of an observer's eyes. It will be appreciated that the observer's eyes are positioned across an interface 148C between the reflective surfaces 148A, 148B to cause the image associated with the right optical image to be observed by the observer's right eye and the image associated with the left optical image to be observed by the observer's left eye. It will be appreciated that the direction of view in FIG. 5 of an observer is normal to the page. Naturally it will be appreciated that FIG. 5 is a schematic diagram and that the viewer 148 can be positioned in any appropriate manner relative to the monitors 144, 146 so that the direction of view of an observer need not be normal to the page as indicated, but can be in a direction toward the monitors 144, 146 for example. Furthermore, the monitors 144, 146 can be positioned at any appropriate position relative to each other and the rest of the system, in which case the optical paths 144C, 146C can be tailored to direct the images from the monitors to the viewer.

Figure 8:
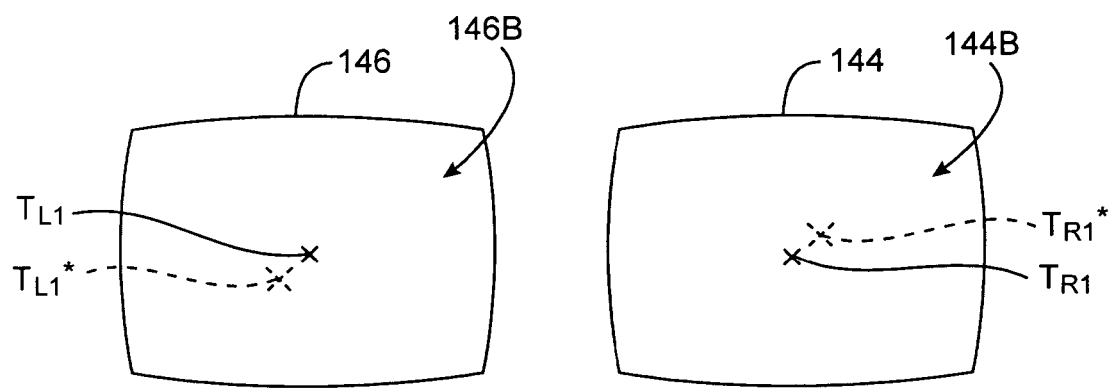
FIG. 8 shows a schematic diagram of two images displayed on a stereo viewer assembly of the system shown in FIG. 5, the images having been derived from the digital information arrays shown in FIG. 7.
Figure 9:
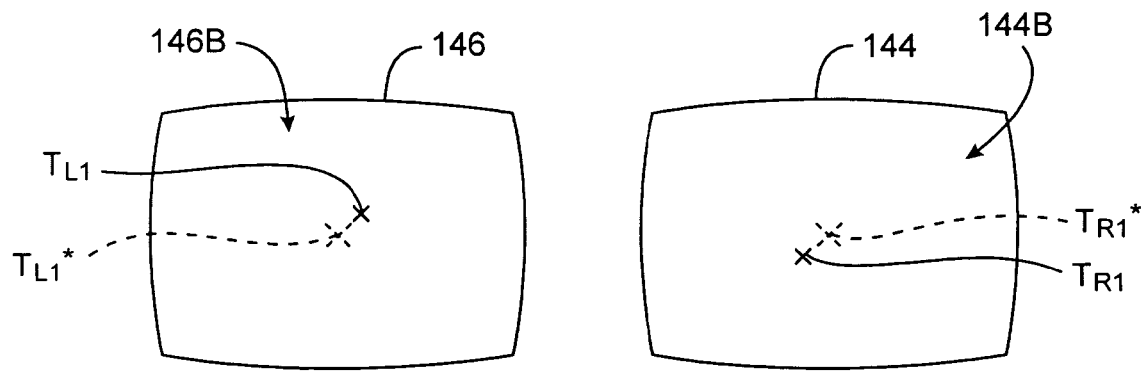
FIG. 9 shows a schematic diagram of two images displayed on the stereo viewer assembly, the images having been derived from isolated portions of the digital information arrays of FIG. 7 to compensate for misalignment in the system.

It would be advantageous to present an optically correct stereo image to the observer. To approach such an optically correct stereo image, it would be advantageous if the system 110 is enabled to compensate for certain optical inaccuracies or shortcomings which may be present in the system. One such shortcoming could arise due to optical misalignment between the optical paths 122, 124 downstream of the CCDs 126, 128. Such misalignment can arise due to lens misalignment, for example. The preferred system 110 provides means for compensating for such misalignment which will now be described with reference to FIGS. 7 to 9 of the drawings.

Figure 7:
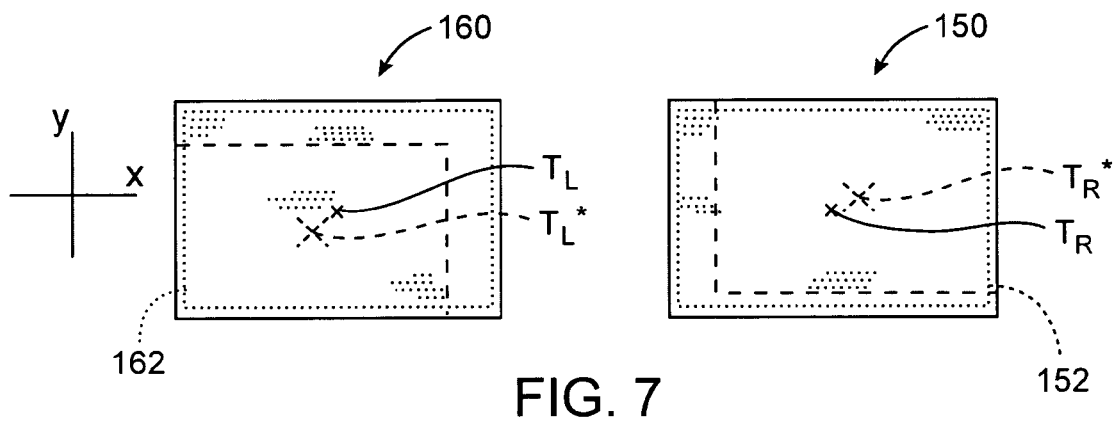
FIG. 7 shows a schematic plan view of two digital information arrays of the system shown in FIG. 5.

Referring initially to FIG. 7 of the drawings, a digital information array associated with the right optical image is generally indicated by reference numeral 150 and a digital information array associated with the left optical image is generally indicated by reference numeral 160. As mentioned hereinbefore, the digital information arrays 150, 160 were derived at the stage 140 as indicated in FIG. 5 of the drawings. It will be appreciated that the images displayed on the monitors 144, 146, shown in FIG. 5 of the drawings, are derived from the digital information contained in the arrays 150, 160. Referring to FIG. 5 of the drawings, means of the system 110 to compensate for misalignment includes a controller 149, which cooperates with the arrays 150, 160. The controller 149 cooperating with the arrays 150, 160 enables discrete portions of the arrays 150, 160 to be isolated so that the images displayed on the monitors 144, 146 are derived from the isolated portions of the arrays 150, 160 only.

It will be appreciated that in an optically aligned system, a target site indicated at T in FIG. 5 of the drawings would be transformed into associated digital information as indicated by the crosses at TR, TL in the digital arrays 150, 160 in FIG. 7. If all the digital information of the arrays 150, 160 is then used to form the images on the displays 144B, 146B of the monitors 144, 146, then the target site T would be positioned generally at centrally disposed positions in the images displayed on the monitors 144, 146 as indicated by TR1, TL1 in FIG. 8 of the drawings. In the case of optical misalignment, the information associated with the target site T on the arrays 150, 160 would be offset as indicated, by way of example, by the dashed crosses TR* and TL* in FIG. 7. Naturally, if all the information of the arrays 150, 160 is then used to form the images on the monitors 144, 146 the target site T would appear at centrally offset positions indicated at TR1* TL1* in FIG. 8, for example.

By enabling the system 110 to isolate portions of the arrays 150, 160 and to cause only such portions to define the information from which the images on the monitors 144, 146 are derived, the misalignment can be compensated for. Accordingly, referring to FIG. 7 of the drawings, given the misalignment as indicated at TR*, TL* described above, the images on the monitors 144, 146 can be aligned by selecting and isolating the portions in dashed lines indicated by reference numerals 152, 162, respectively, and using only this information to derive the images displayed on the monitors 144, 146. In such a case, the digital information relating to the target site T, in the case of misalignment, namely at $TR_1^*$, $TL_1^*$, would then be imaged at centrally disposed positions on the monitors 144, 146 as indicated by $TR_2^*$, $TL_2^*$ in FIG. 9 of the drawings. In this way, the misalignment of the optical paths 122, 124 is compensated for. It will be appreciated that not only misalignment which can arise in the optical paths 122, 124 can be compensated for in this manner, but misalignment elsewhere also, such as between the CCDs 126, 128 and the CCUs 130, 132, for example.

To assist in the alignment process described above, use is typically made of a target device schematically indicated at 121 in FIG. 5 of the drawings. The target device is shown schematically in greater detail, and on an enlarged scale, in FIGS. 11 and 12 of the drawings. The target device 121 is in the form of a cap releasably mountable on the viewing end 112A of the endoscope 112 as indicated in FIG. 5 of the drawings. The target device includes a body 121.1 The body 121.1 defines an internal seat 121.2 extending along an internal periphery 121.3, whereby it can be mounted on the viewing end of the endoscope by positioning the viewing end 112A of the endoscope 112 in the seat 121.2 thereby frictionally to engage over said end 112A.

The target device 121 further includes a target 121.4 opposed from the seat 121.2. The target 121.4 is at a fixed distance W from the seat 121.2. The target 121.4 is shaped in the form of a cross. However, it will be appreciated that any suitably shaped target can be used instead, e.g., a centrally disposed circle, or the like.

Figure 6:
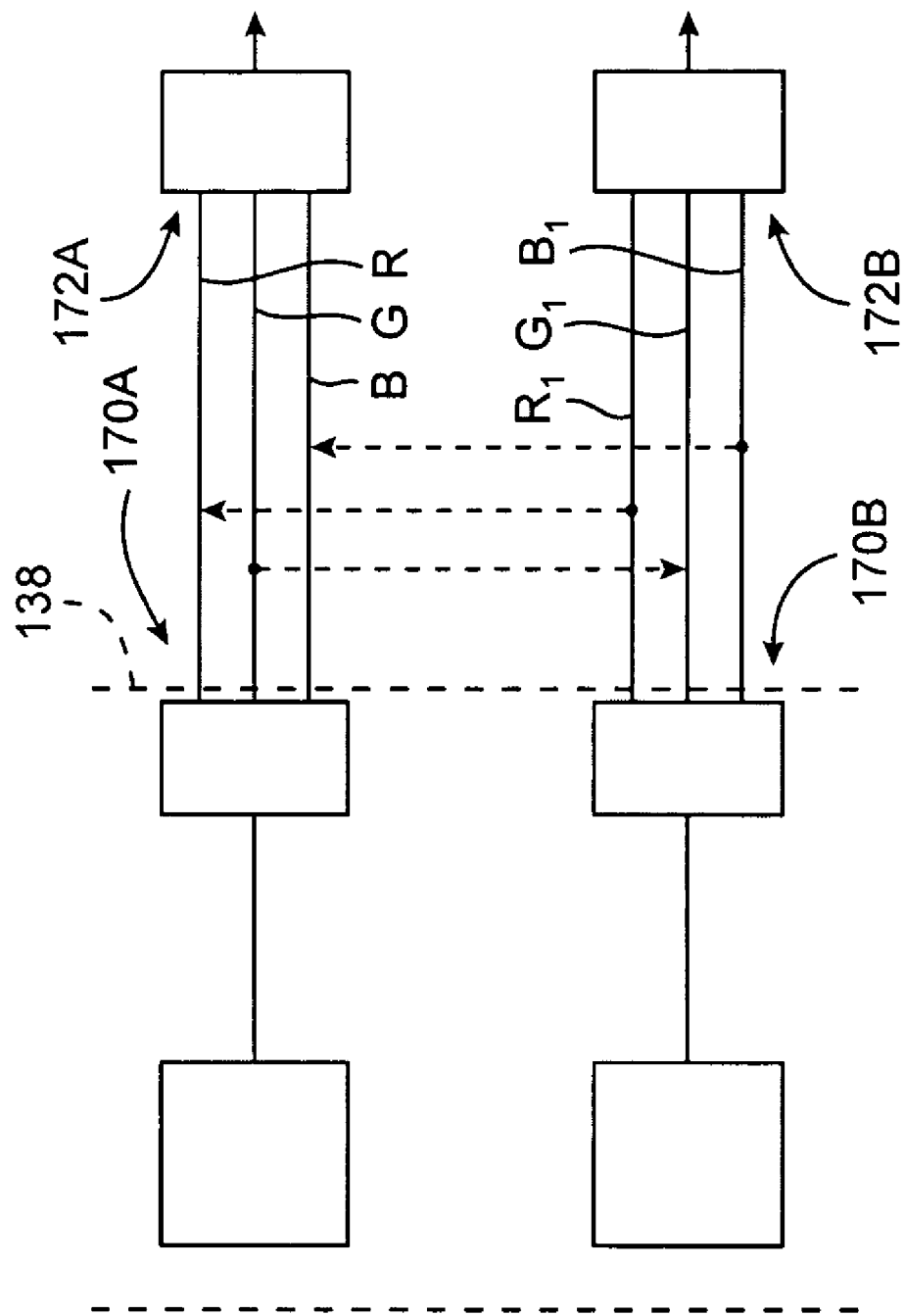
FIG. 6 shows a schematic diagram of part of the system shown in FIG. 5 and further indicates steps involved in a method of aligning the viewing axes of an endoscope of the system, in accordance with the invention.

To assist the alignment process, and as represented in FIG. 6 of the drawings, outputs from the video processor 138 as indicated generally at 170A, 170B which are normally operatively connected to inputs 172A, 172B associated with the monitors 144, 146, are interchanged so as to cause each image displayed on the monitors 144, 146 to be a mix of the information associated with both paths 122, 124. The outputs at 170A, 170B are associated with conventional red, green, and blue signals as indicated by the letters R, G, B and $R_1$, $G_1$, $B_1$, respectively. The outputs 170A, 170B are normally operatively connected to the inputs 172A, 172B as indicated by the solid parallel lines. To interchange the outputs, the $R_1$ signal is routed to the R input, the $B_1$ signal is routed to the B input and the G signal is routed to the $G_1$ input. Accordingly, in this manner, the image displayed on each viewer 144, 146 is in the form of a composite image associated with both optical images 122, 124. Conveniently, to enable each image of the composite image to be readily distinguished, the images are caused to have different distinct colors, e.g., green and magenta, or the like.

Figure 10:
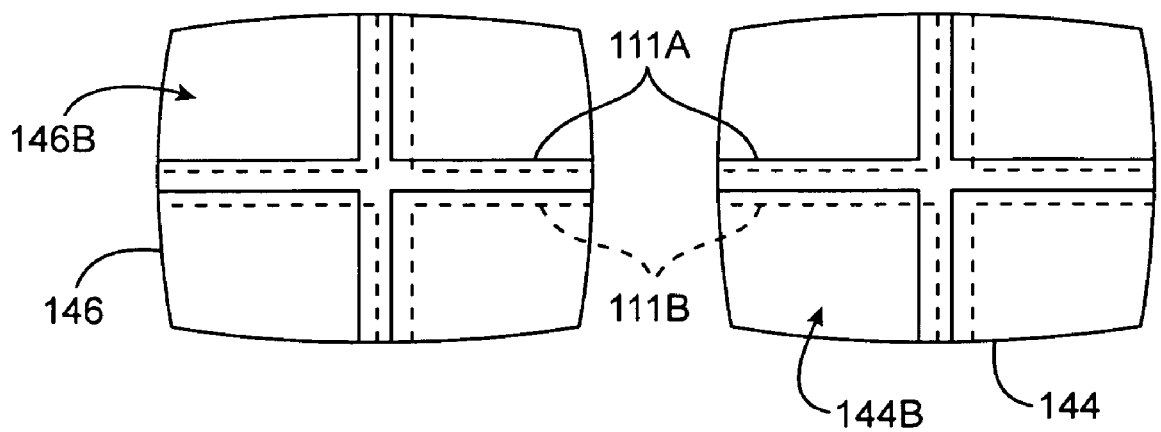
FIG. 10 shows a schematic diagram of two images displayed on the stereo viewer assembly, the images being associated with a target used to assist in compensating for misalignment in the system.

When the target device is mounted on the viewing end 112A of the endoscope 112 and the outputs 170A, 170B and the inputs 172A, 172B are interchanged in this fashion, the target, i.e., the cross, in the case of misalignment, is displayed in a misaligned manner on each monitor 144, 146 as indicated schematically by the solid lines 111A and dashed lines 111B, respectively, in FIG. 10 of the drawings. The controller shown in FIG. 5 is then used to select portions of the arrays 150, 160 which would cause the targets as viewed on the monitors 144, 146 to be superimposed or in register. This is typically achieved by the observer while viewing the images at the viewer 148 and manipulating an input 151 operatively linked to the controller 169 as indicated in FIG. 5. The input can be in any appropriate form such as opposed vertical and horizontal switches, foot pedals, voice commands, or the like. Typically, opposed vertical and horizontal switches are used so that when an upper of the vertical switches is depressed, a center of a portion of the one digital array 150, 160 is caused to move progressively upwardly and a center of a portion of the other digital array 150, 160 is caused to move progressively downwardly. Similarly if the lower vertical switch is depressed, the center of the portions selected move progressively in directions opposite to the directions of the movement when the upper vertical switch is depressed. Naturally, when the one horizontal switch is depressed, centers of the portions selected move progressively toward each other, and when the other horizontal switch is depressed, the center of the portions selected move progressively laterally away from each other. The switches are operated in this manner until the images of the composite image on the viewers 144, 146 are superimposed or in register. The system 110 is then set so that the selected isolated portions of the arrays 150, 160 which cause the images to be aligned are retained thereby to compensate for misalignment.

It will be appreciated that instead of selecting portions of the arrays 150, 160, the arrays 150, 160 can be arranged to form parts of larger arrays (not shown). Alignment can then be established in similar fashion, but by moving the arrays 150, 160 as a whole relative to the larger arrays. It will further be appreciated that the controller 149 can be arranged to select and isolate a portion of only one of the arrays 150, 160 to establish alignment. It will yet further be appreciated that once alignment has been achieved, conventional connection between outputs 170A, 170B and corresponding inputs 172A, 172B is re-established.

Once misalignment has been compensated for, working distance variation is achieved in similar fashion, except that portions of the digital arrays 150, 160 are selected and isolated which have centers closer to each other in an X direction as indicated by the coordinate reference frame 161 in FIG. 7 of the drawings, to increase the working distance and portions having centers further removed in an X direction are isolated to decrease the working distance. It will be appreciated that during the misalignment compensation procedure described above the isolated portions can vary in an X and Y direction whereas once alignment is achieved, working distance variation is achieved by isolating portions such that the distance between their centers varies along the X axis only. Furthermore, when misalignment compensation is achieved using the target device 121, the working distance is typically at a distance corresponding to the distance between the target cross and the viewing end 112A of the endoscope. Thereafter, varying the working distance can typically be achieved by a suitable input indicated at 153 in FIG. 5 of the drawings. The suitable input can be in any appropriate form such as a hand operable switch, depressible foot pedal, or the like. Typically, the input can be arranged to cause stepwise adjustment of preset working distances. Accordingly, a plurality, e.g., three, settings can be provided to vary the working distance between three preset distances.

Referring now to FIGS. 13 to 16 of the drawings, another method of aligning opposed images of a stereo imaging system will now be described.

Figure 13:
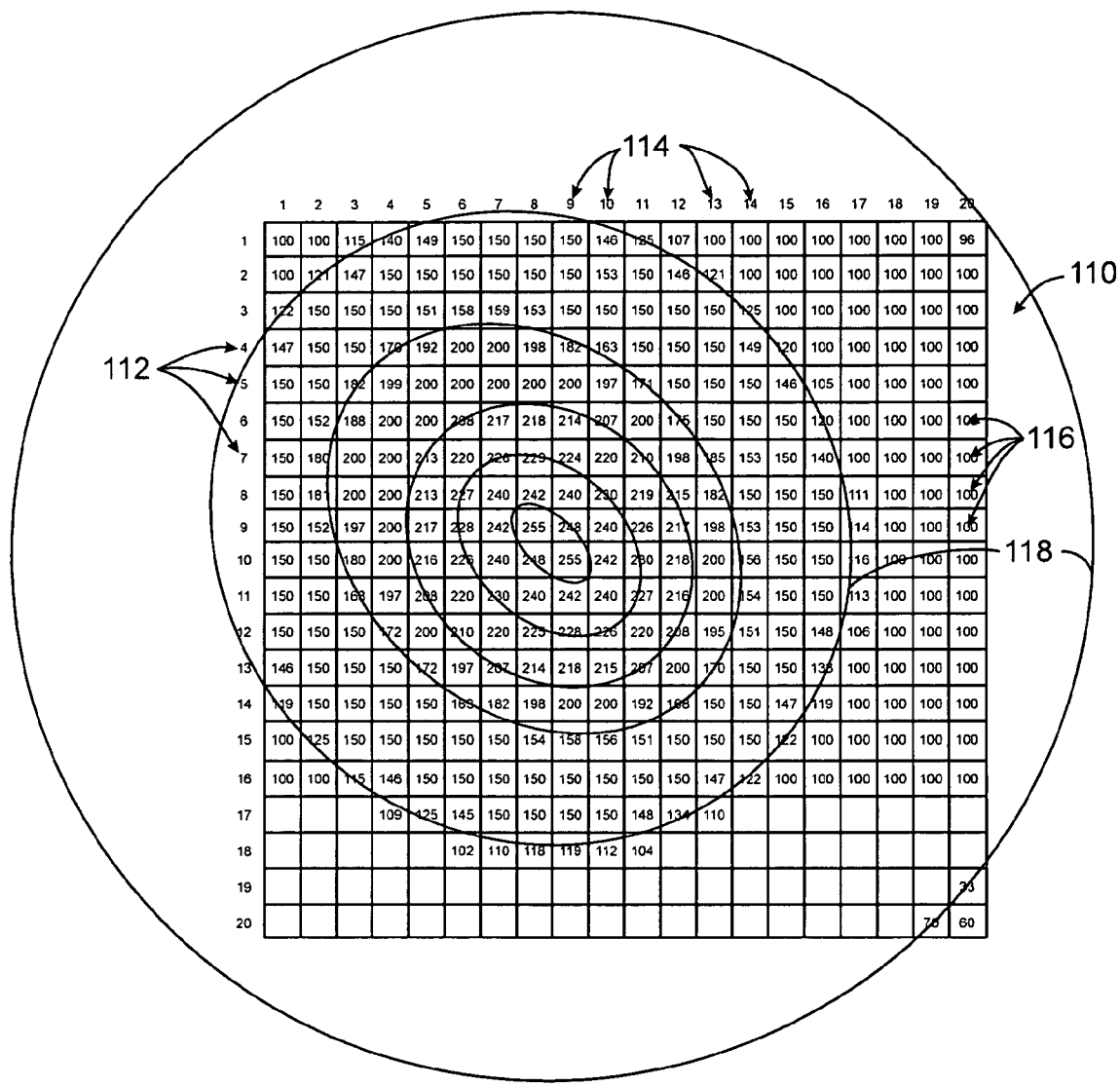
FIG. 13 shows a digital array of one of a right and left optical image.

Referring initially to FIG. 13 of the drawings, a digital array is generally indicated by reference numeral 110. It will be appreciated that the digital array 110, is shown to be a 20×20 array for illustrative purposes only. Typically, a 64×64 array can be used. The array 110 includes a plurality of rows 112. It further includes a plurality of columns 114. The rows 112 and columns 114 define discrete locations 116 in which numerical values relating to pixel information of a captured image is contained. For illustrative purposes only, a series of elliptical rings 118 is shown superimposed on the array 110. The series of elliptical rings 118 represent a target viewed by the endoscope and from which the digital information in the array 110 was derived. Toward a central position of the elliptical rings the numerical values contained in the rows 112 and columns 114 are of higher numerical value than in the peripheral regions. Accordingly, the target viewed by the endoscope has a brighter portion corresponding to the centrally disposed position of the elliptical rings 118 than at a position away from the centrally disposed position.

Figure 11:
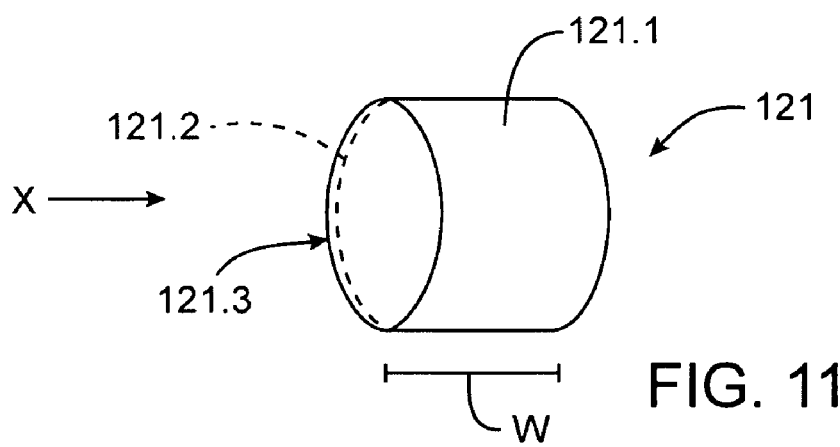
FIG. 11 shows a schematic three-dimensional view of a target device used to assist in compensating for the misalignment in the system.
Figure 12:
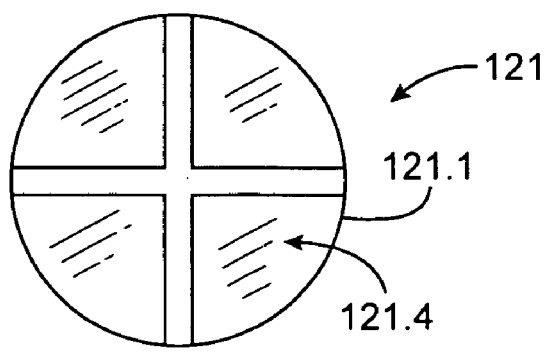
FIG. 12 shows a plan view of the target device along arrow X in FIG. 11 and shows the target viewed in the images shown in FIG. 10.

It will be appreciated that although, for the sake of example, reference is made to elliptical rings 118, the target as described with reference to FIGS. 11 and 12 may be used instead. It will further be appreciated that the digital array 110 is only one digital array corresponding to either the left or the right optical image captured by the endoscope. Accordingly, when a target site is viewed by the endoscope, a digital array corresponding to digital array 110 would be captured for each of the left and the right optical images.

When the digital arrays for the left and the right optical images have been captured in this fashion, any misalignment in the system can be compensated for automatically. A method for automatically compensating for misalignment will now be described in further detail. Once the digital arrays have been captured a processor analyzes each row 112 to determine the highest numerical value in that row. Once the highest numerical value in a particular row has thus been determined, that maximum value is multiplied by a predetermined constant. Typically, the predetermined constant can have a value ranging between about 0.7 and 0.95. A value often used is 0.9. Once the maximum numerical value has been multiplied by the predetermined constant a threshold value for that row is defined. The processor then scans the row and determines the location of the first numerical value which exceeds the threshold value as well as the location of the last numerical value which exceeded the threshold value. In this manner, two opposed locations are determined in the row. The processor then determines the mean location between these locations.

The above procedure is repeated for each row 112. Thus, a location in each row 112 is determined which corresponds to the mean between the first and the last value which exceeded the threshold value for each specific row. The same method is employed for each column 114. Accordingly, a location in each column is determined which represents the mean between the locations of the first and the last numerical values in that column which exceeded the threshold value determined for that column.

Figure 14:
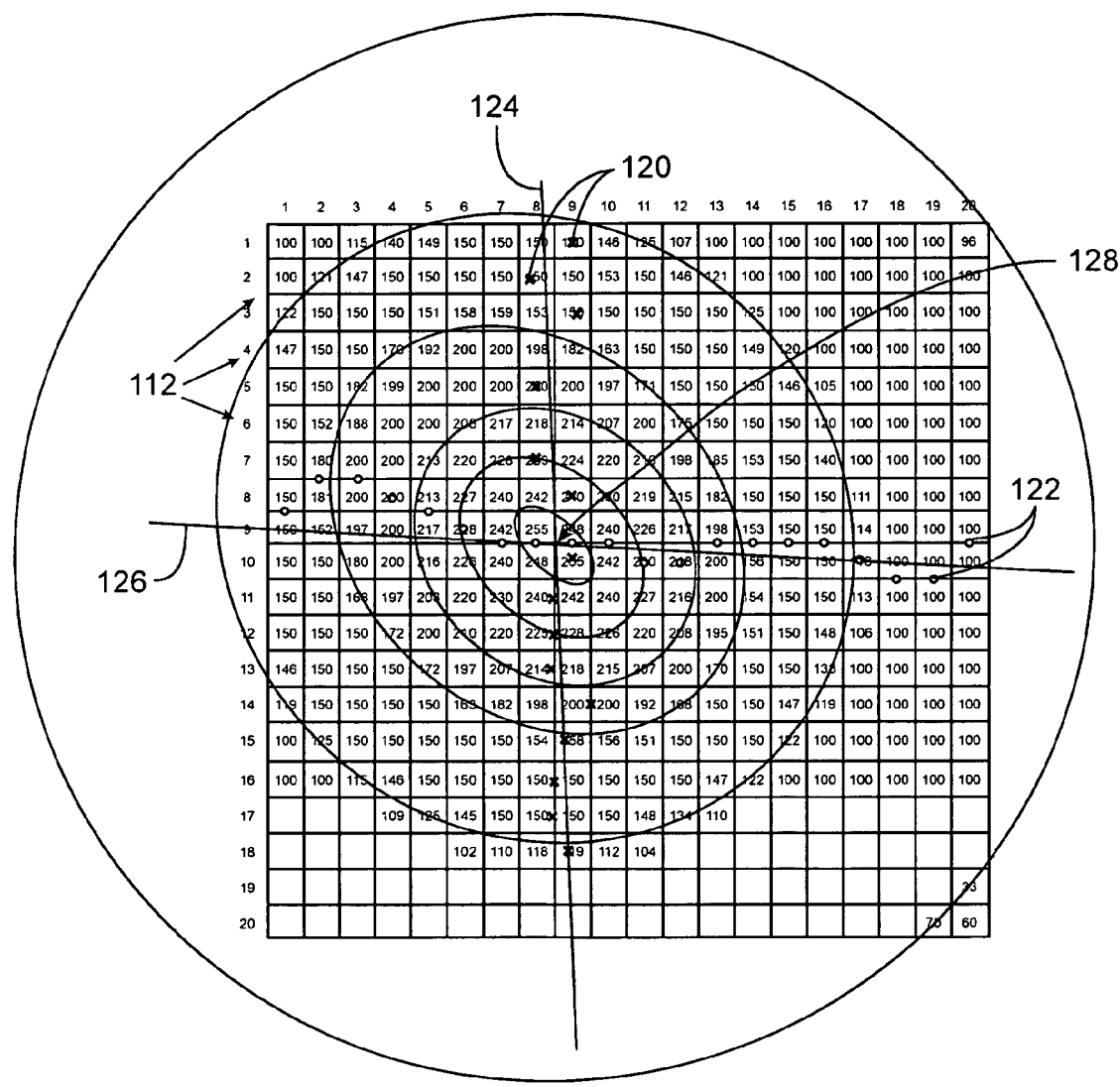
FIG. 14 shows the digital array of FIG. 13, and further shows a least squares fit to columns and rows of the digital array, where the least squares fit has been computed based on the mean between the locations of a first and a last thresholded maximum value for each row and column.

Referring now to FIG. 14, the mean values determined as described above for each row 112 is indicated by the crosses 120. Similarly, the mean values for each column is indicated by the circles 122. The processor then computes a least squares fit using the locations of the mean values. The results of this computation is indicated by the straight lines 124 and 126, respectively. The location of the intersection between these lines, indicated at 128, is then determined.

It will be appreciated that the location of the mean value for every single row and column need not necessarily be determined. Instead, only the locations of the mean values of predetermined spaced-apart rows and columns can be determined. Accordingly, the location of the mean value of every second, third, fourth or the like, row and column can be determined to provide adequate data to determine the intersections 128 for each digital array.

Figure 15:
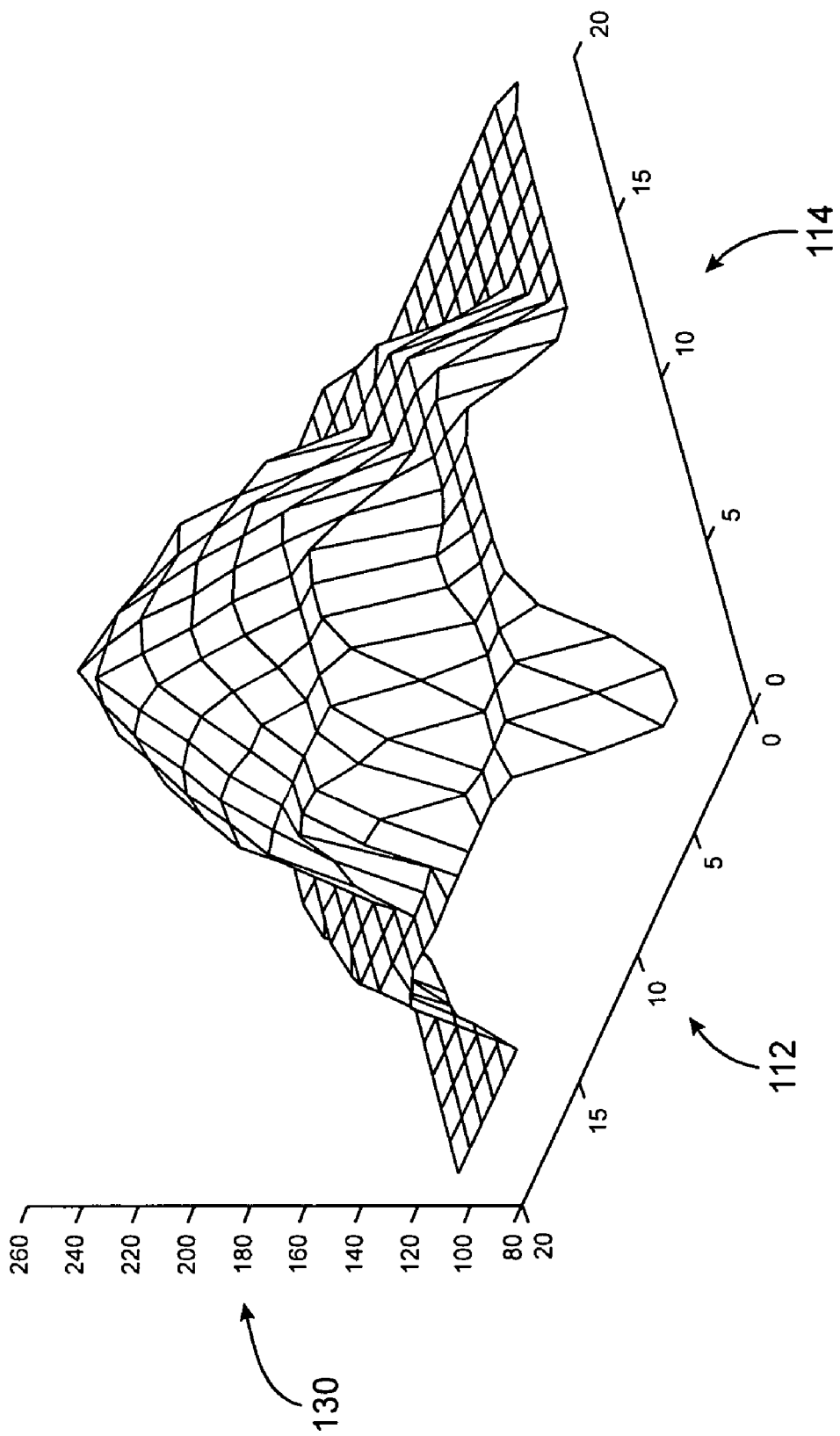
FIG. 15 shows a graphical representation of digital values in the rows and columns of FIGS. 13 and 14.
Figure 16:
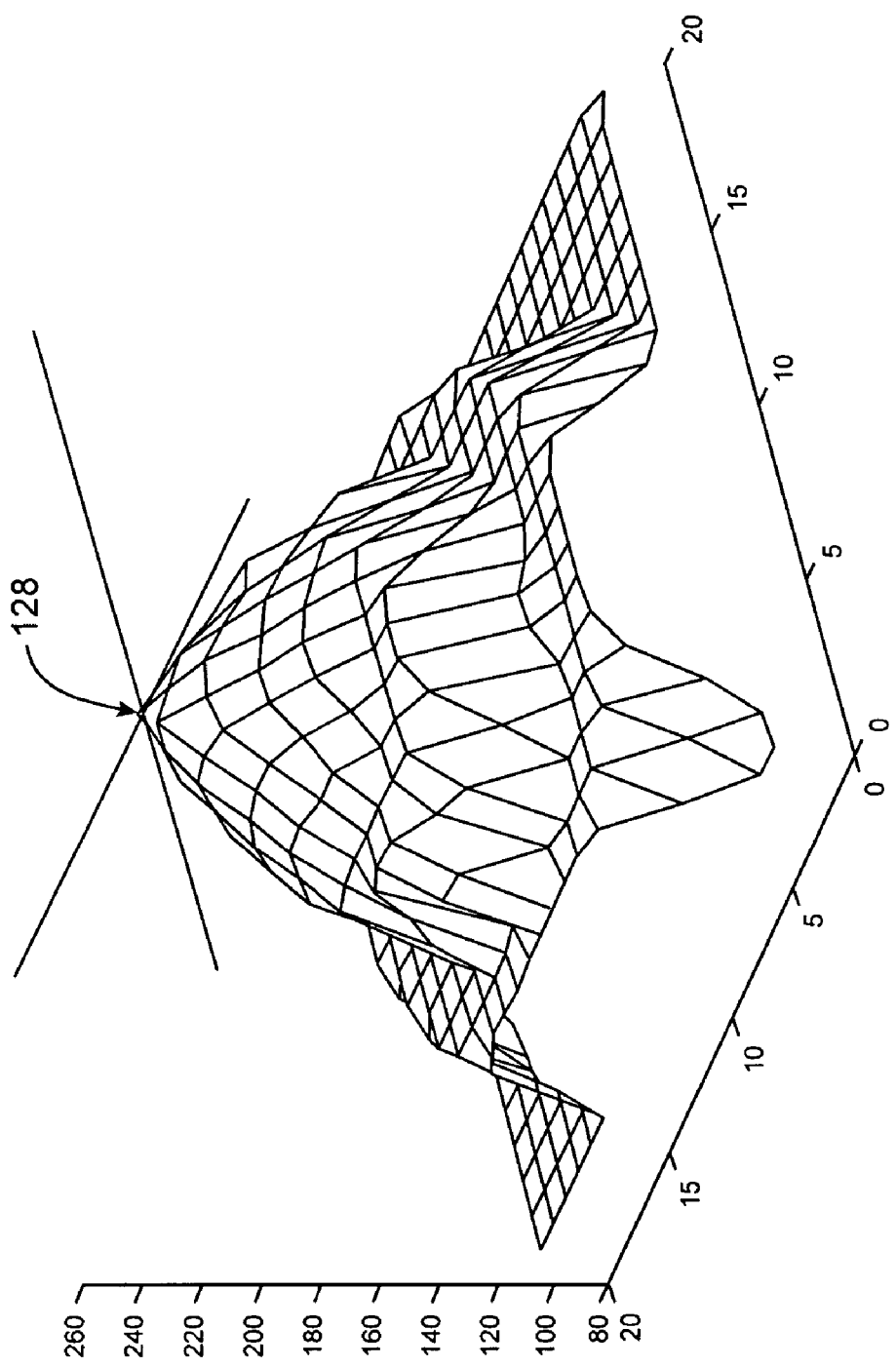
FIG. 16 shows a position of an intersection between the least squares fit for the rows and columns, superimposed on the graphical representation of FIG. 15.

Referring to FIG. 15, a graphical representation of the numerical values in the rows 112 and columns 114, is diagrammatically indicated in a three dimensional format. The numerical values are indicated at 130. When the computations as described above have been completed, the intersection 128 indicated in FIG. 14 corresponds generally to the position within the digital array 110 corresponding to a maximum numerical value. This can best be seen with reference to FIG. 16 in which the lines 124, 126 have been superimposed on the diagram of FIG. 15.

Once the locations of the intersections between lines 124 and 126 have been determined in the digital array corresponding to each of the left and the right optical images, the processor selects portions or cropping windows of each of the digital arrays such that the location of the intersections 128 for each array occupy the same position relative to the selected portions or cropping windows. Only digital information relating to the selected portions is then used to display an image on the viewer corresponding to the left and the right optical images respectively to align the images.

It will be appreciated that to compensate for misalignment as described above, use can be made of an appropriate target device as described earlier in this specification. However, as those skill in the art will be aware, compensation for misalignment using this method can be accomplished without use of a target device. In such a case, where use is not made of a target device, the endoscope can be directed to capture any appropriate image, such as of the surgical site on which it is intended to perform a surgical procedure, and use can then be made of appropriate pattern matching templates, or the like, to determine intersections as described above for the digital arrays corresponding to the image of the surgical site. Furthermore, it will be appreciated that the system can be arranged automatically to compensate for misalignment as described above periodically. Furthermore, it is to be appreciated that the compensation for misalignment when performed periodically can be arranged to compensate for vertical alignment between the images only, so that if the surgeon has selected a particular working distance, that working distance is maintained.

Referring again to FIG. 5 of the drawings, the system 110 is provided with a focusing arrangement generally indicated by reference numeral 180. The arrangement 180 is arranged to move the lenses 118, 120 selectively in the direction indicated by arrows 182. This is achieved by means of an electric motor 184 operatively associated with the lenses 118, 120 through an appropriate transmission, e.g., gears, or cable and pulley arrangements, or rack and pinion arrangements, or the like. The motor 184 is driven by means of a focus controller 186. The focus controller is typically connected to an input device at the operator console. The input device can be in any appropriate form, e.g., switches, knobs, voice control, or the like. Accordingly, an operator can adjust the focus by means of the input device.

While exemplary preferred embodiments have been described in some detail, for purposes of clarity of understanding and by way of example only, a variety of changes, modifications, and adaptations will be obvious to those skilled in this art. Accordingly, the scope of the present invention is reflected by the appended claims. Thus, while the preferred embodiments of the present invention are described as including converting the various optical images into regulatable information in the form of digital information, other forms of regulatable information, such as analog information, could be used instead, as will be apparent to one of ordinary skill in the art upon reading this disclosure. For example, to vary the position of the images displayed on the monitors to vary the working distance, regulatable information including a sync signal and a video signal for input to the respective monitors can be regulated so as to skew the sync and video signals relative to each other and a blanking system of the monitors can be permitted to select active pixels to provide such working distance variation or compensation for misalignment.

What is claimed is:

1. A method of aligning left and right stereoscopic images, the method comprising:
   capturing right stereoscopic image pixel information for a target object in a first array;
   capturing left stereoscopic image pixel information for the target object in a second array;
   calculating a first intersection position in the first array by:
      for each of a plurality of rows in the first array, determining a first pixel column position that exceeds a row threshold value, a last pixel column position that exceeds the row threshold value, and a column position between the first pixel column position and the last pixel column position;
      for each of a plurality of columns in the first array, determining a first pixel row position that exceeds a column threshold value, a last pixel row position that exceeds the column threshold value, and row position between the first pixel row position and the last pixel row position; and
      determining a position at which a first line fitted to the column positions between the first pixel column positions and the last pixel column positions intersects a second line fitted to the row positions between the first pixel row positions and the last pixel row positions;
   calculating a second intersection position in the second array;
   selecting a portion of the first array and a portion of the second array such that the calculated intersection positions for each array substantially occupy the same position relative to the selected portions; and
   outputting an aligned stereoscopic image to a viewer by displaying the selected portion of the first array and the selected portion of the second array.

2. The method of claim 1, wherein the column position between the first pixel column position and the last pixel column position is based on a mean value of pixel values between the first pixel column position and the last pixel column position.

3. The method of claim 1, wherein:
   the plurality of rows comprises all rows in the array; or
   the plurality of columns comprises all columns in the array; or
   the plurality of rows comprises all rows in the array and the plurality of columns comprises all columns in the array.

4. The method of claim 1, wherein:
   the column position between the first pixel column position and the last pixel column position is based on a mean value of pixel values between the first pixel column position and the last pixel column position; or
   the row position between the first pixel row position and the last pixel row position is based on a mean value of pixel values between the first pixel row position and the last pixel row position; or
   the column position between the first pixel column position and the last pixel column position is based on a mean value of pixel values between the first pixel column position and the last pixel column position, and the row position between the first pixel row position and the last pixel row position is based on a mean value of pixel values between the first pixel row position and the last pixel row position.

5. A method of aligning left and right stereoscopic images, the method comprising:
   capturing right stereoscopic image pixel information for a target object at a surgical site in a first array;
   capturing left stereoscopic image pixel information for the target object in a second array;
   calculating a first line position in the first array;
   calculating a second line position in the second array;
   selecting a portion of the first array and a portion of the second array such that the calculated line positions for each array substantially occupy the same position relative to the selected portions;
   outputting an aligned stereoscopic image to a viewer by displaying the selected portion of the first array and the selected portion of the second array; and
   maintaining a selected working distance of an endoscope used to capture the right and left stereoscopic image pixel information by periodically repeating the acts of capturing right stereoscopic image pixel information, capturing left stereoscopic image pixel information, calculating a first line position, calculating a second line position, selecting a portion of the first array and a portion of the second array, and outputting an aligned stereoscopic image.

6. The method of claim 5, wherein calculating the first line position comprises:
   for each of a plurality of rows in the first array, determining a first pixel column position that exceeds a row threshold value, a last pixel column position that exceeds the row threshold value, and a column position between the first pixel column position and the last pixel column position; and
   fitting the first line to the column positions between the first pixel column positions and the last pixel column positions.

7. The method of claim 6, wherein the column position between the first pixel column position and the last pixel column position is based on a mean value of pixel values between the first pixel column position and the last pixel column position.

8. The method of claim 6, wherein the plurality of rows comprises all rows in the array.

9. The method of claim 5, wherein calculating a first line position comprises using a pattern matching template for the first array, and wherein the first array pixel information corresponds to an image of a surgical site.

10. An endoscopic imaging system comprising:
an image capture stage that captures right stereoscopic image pixel information for a target object in a first array and left stereoscopic image pixel information for the target object in a second array;
a video processing stage that
  calculates a first intersection position in the first array and a second intersection position in the second array, wherein calculating the first intersection position comprises:
    for each of a plurality of rows in the first array, determining a first pixel column position that exceeds a row threshold value, a last pixel column position that exceeds the row threshold value, and a column position between the first pixel column position and the last pixel column position;
    for each of a plurality of columns in the first array, determining a first pixel row position that exceeds a column threshold value, a last pixel row position that exceeds the column threshold value, and row position between the first pixel row position and the last pixel row position; and
  determining a position at which a first line fitted to the column positions between the first pixel column positions and the last pixel column positions intersects a second line fitted to the row positions between the first pixel row positions and the last pixel row positions, and
  selects a portion of the first array and a portion of the second array such that the calculated intersection positions for each array substantially occupy the same position relative to the selected portions; and
a monitor stage that outputs an aligned stereoscopic image to a viewer by displaying the selected portion of the first array and the selected portion of the second array.

11. The system of claim 10, wherein the target object comprises an object at a surgical site on which a surgical procedure is performed.

12. The system of claim 10, wherein the column position between the first pixel column position and the last pixel column position is based on a mean value of pixel values between the first pixel column position and the last pixel column position.

13. The system of claim 10, wherein:
the plurality of rows comprises all rows in the array; or
the plurality of columns comprises all columns in the array; or
the plurality of rows comprises all rows in the array and the plurality of columns comprises all columns in the array.

14. The system of claim 10, wherein:
the column position between the first pixel column position and the last pixel column position is based on a mean value of pixel values between the first pixel column position and the last pixel column position; or
the row position between the first pixel row position and the last pixel row position is based on a mean value of pixel values between the first pixel row position and the last pixel row position; or
the column position between the first pixel column position and the last pixel column position is based on a mean value of pixel values between the first pixel column position and the last pixel column position and the row position between the first pixel row position and the last pixel row position is based on a mean value of pixel values between the first pixel row position and the last pixel row position.

15. The system of claim 10, wherein calculating a first intersection position comprises using a pattern matching template for the first array, and wherein the first array pixel information corresponds to an image of a surgical site.

16. The system of claim 10, wherein the acts of capturing right stereoscopic image pixel information, capturing left stereoscopic image pixel information, calculating a first intersection position, calculating a second intersection position, selecting a portion of the first array and a portion of the second array, and outputting an aligned stereoscopic image are automatically repeated to compensate for stereoscopic image misalignment.

17. The system of claim 10 further comprising an endoscope through which the right stereoscopic image and the left stereoscopic image are transmitted to the image capture stage.

* * * * *